US012790376B2

(12) United States Patent
Nigro et al.

(10) Patent No.: US 12,790,376 B2
(45) Date of Patent: Nov. 10, 2026

(54) DEFENSIN-DERIVED PEPTIDE WITH ANTIBACTERIAL ACTIVITY ALSO AGAINST MULTI-ANTIBIOTIC-RESISTANT BACTERIA

(71) Applicant: CEINGE BIOTECNOLOGIE AVANZATE FRANCO SALVATORE S.C. A R.L., Naples (IT)

(72) Inventors: Ersilia Nigro, Caserta (IT); Irene Colavita, San Paolo Bel Sito (IT); Roberta Colicchio, Naples (IT); Aurora Daniele, Naples (IT); Paola Salvatore, Naples (IT); Antonello Pessi, Rome (IT); Francesco Salvatore, Poggio Ravaschieri Vomero (IT)

(73) Assignee: CEINGE BIOTECNOLOGIE AVANZATE FRANCO SALVATORE S.C. A R.L., Naples (IT)

( * ) Notice: Subject to any disclaimer, the term of this patent is extended or adjusted under 35 U.S.C. 154(b) by 369 days.

(21) Appl. No.: 18/703,408

(22) PCT Filed: Oct. 26, 2022

(86) PCT No.: PCT/IB2022/060288
§ 371 (c)(1),
(2) Date: Apr. 22, 2024

(87) PCT Pub. No.: WO2023/073577
PCT Pub. Date: May 4, 2023

(65) Prior Publication Data

US 2024/0417435 A1 Dec. 19, 2024

(30) Foreign Application Priority Data

Oct. 27, 2021 (IT) ........................ 102021000027581

(51) Int. Cl.
*C07K 14/47* (2006.01)
*A61K 38/00* (2006.01)
*A61P 31/04* (2006.01)

(52) U.S. Cl.
CPC .......... *C07K 14/4723* (2013.01); *A61P 31/04* (2018.01); *A61K 38/00* (2013.01)

(58) Field of Classification Search
CPC ...... C07K 14/4723; A61P 31/04; A61K 38/00
See application file for complete search history.

(56) References Cited

FOREIGN PATENT DOCUMENTS

| | | | |
|---|---|---|---|
| EP | 2077274 | A1 | 7/2009 |
| EP | 2990415 | A1 | 3/2016 |

OTHER PUBLICATIONS

Bai Y et al., "Structure-depedent charge density as a determinant of antimicrobial activity of peptide analogues of defensin", Biochemistry, vo. 48, No. 30, Aug. 4, 2009, pp. 7229-7239.
Dhople V et al., "the human beta-defensin-3, an antibacterial peptide with multiple biological functions", Biochimica et Biophysica Acta, vol. 1758, No. 9, Jul. 21, 2006, pp. 1499-1512.
Hoove D M et al, "Antimicrobial characterization of human beta-defensin 3 derivatives", Antimicrobial Agents and Chemotherapy, vol. 47, No. 9, Sep. 1, 2003, pp. 2804-2809.
Papanastasiou E A et al., "Role of acetylation and charge in antimicrobial peptides based on human [beta]-defensin-3: Potency & Small Cationic Peptides", APMIS, vol. 117, No. 7, Jun. 23, 2009, pp. 492-499.
Sakagami-Yasui Yoko et al., "Two arginine residues in the COOH-terminal of human [beta]-defensin-3 constitute an essential motif for antimicrobial activity and IL-6 production", Experimental Dermatology, vol. 26, No. 11, Apr. 18, 2017, pp. 1026-1032.
Scudiero O et al., "Chimeric beta-defensin analogs, including the novel 3NI analog, display salt-resistant antimicrobial activity and lack toxicity in human epithelial cell lines", Antimicrobial Agents and Chemotherapy, vo. 57, No. 4, Jan. 28, 2013, pp. 1701-1708.
Scudiero O et al., "Novel synthetic salt-resistant analogs of human beta-defensins 1 and 3 endowed with enhanced antimicrobial activity", Antimicrobial agents and Chemotherapy, vo.. 54, No. 6, Jun. 1, 2010, pp. 2312-2322.
Search Report and Written Opinion of PCT/IB2022/060288 issued Mar. 2, 2023.

*Primary Examiner* — Erinne R Dabkowski
(74) *Attorney, Agent, or Firm* — Silvia Salvadori, P.C.; Silvia Salvadori

(57) ABSTRACT

Disclosed is a synthetic peptide derived from the beta-defensin sequence. The peptide has marked antibacterial activity, in particular against antibiotic-resistant bacteria. The application concerns a modified from of peptide y, derived from human beta-Defensin 3 (hBD3), called "peptide y2" and having the sequence Ac-CLPKRRQIGKSSTRGRKSCKK(SEQ ID NO: 1)-$NH_2$-. The peptide has a more substantial change in the y-core sequence compared to the full-length hBD3 which improves the activity and has a shorter sequence and fewer sites susceptible to cleavage by serum proteins. The peptide is therefore stable in the blood, not cytotoxic, exerts an effective antibacterial capacity against both planktonic and sessile bacteria and shows a bactericidal effect even against Gram-positive and Gram-negative MDR bacterial strains.

4 Claims, 11 Drawing Sheets

Figure 1:
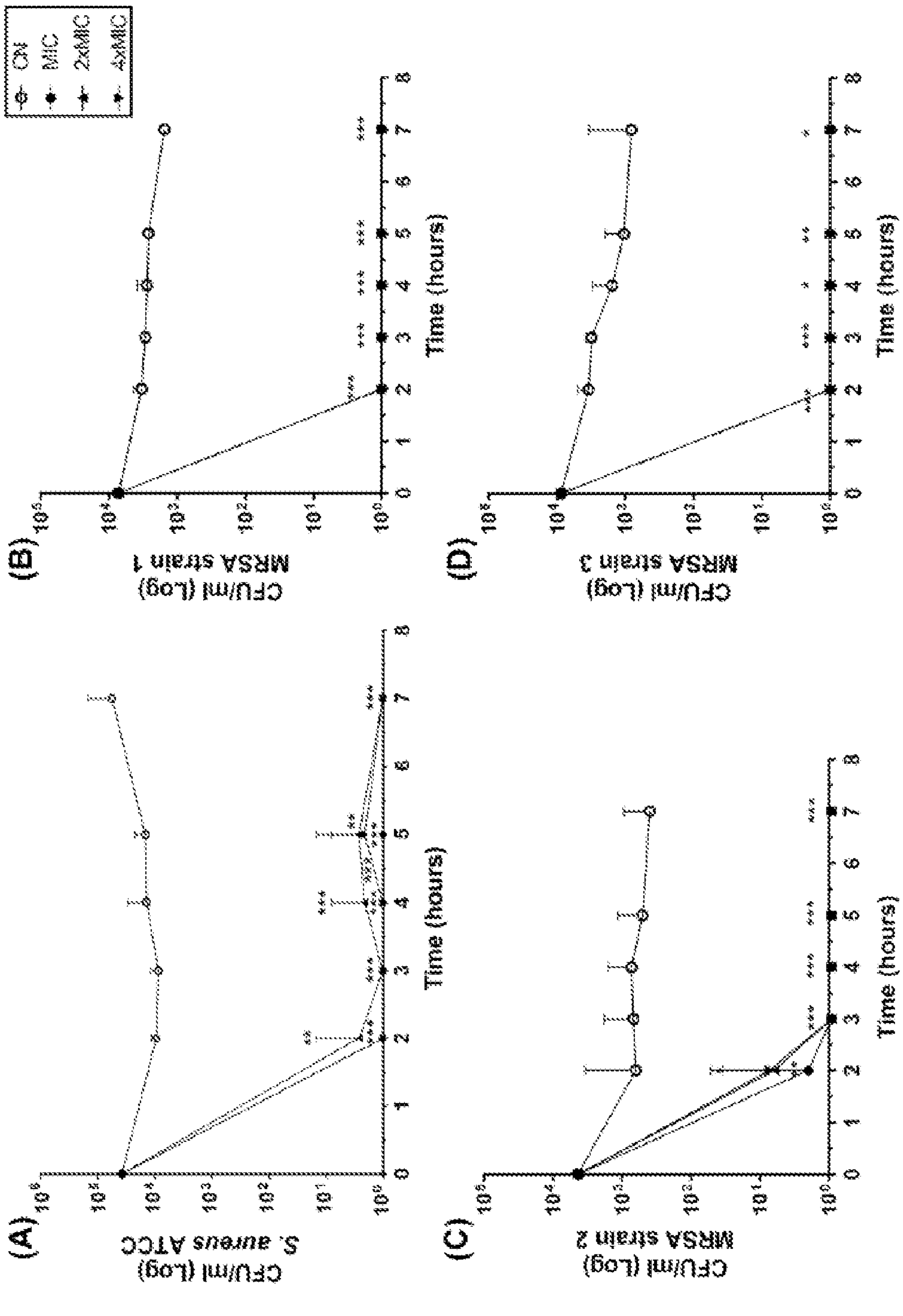

Specification includes a Sequence Listing.

DEFENSIN-DERIVED PEPTIDE WITH ANTIBACTERIAL ACTIVITY ALSO AGAINST MULTI-ANTIBIOTIC-RESISTANT BACTERIA

Sequence listing Sequences.xml, created on Mar. 28, 2024 and of size of 2,517 bytes is incorporated herein by reference.

This application is a U.S. national stage of PCT/IB2022/060288 filed on 28 Oct. 2022, which claims priority to and the benefit of Italian Patent Application No. 102021000027581 filed on 27 Oct. 2021, the contents of which are incorporated herein by reference in their entireties.

The present invention relates to a defensin-derived peptide and the use thereof as antibacterial agent, in particular in the treatment of infections.

INTRODUCTION—STATE OF THE ART

Infections associated with multidrug-resistant (MDR) bacteria, such as methicillin-resistant *Staphylococcus aureus* (MRSA), multidrug-resistant *Pseudomonas aeruginosa* and extended-spectrum beta-lactamase (ESBL)-producing *Escherichia coli*, still represent a major challenge because of the limited treatment options. It is estimated that in Europe alone, there are 171,200 infections associated with MRSA every year, affecting both adults and children. Moreover, high levels of ESBL-producing *E. coli* and increasing frequency of resistance to the main antimicrobials are of serious concern, reflecting a continual loss of efficacy in the treatment of patients with serious infections (such as blood, urinary tract and intra-abdominal infections).

The emergence of said MDR bacterial strains has therefore increased public health costs. The research of more sophisticated methods of treating MDR bacteria effectively is now essential and represents one of the major challenges for the 21st century. Cationic antimicrobial peptides (CAMPs) seem to be promising candidates to overcome resistance (Mandal S M et al., *Front Pharmacol* 2014; 5:105; Guani-Guerra E et al., *Clin Immunol* 2009; 135:1-11).

CAMPs are a large group of natural low-molecular-weight peptides that play an important role in the innate immunity of the majority of living organisms, comprising invertebrates and vertebrates, which are developed as part of the primordial protective immune mechanism (Pazgier M et al., *Cell Mol Life Sci* 2006; 63:1294-1313) with a broad spectrum of activity against Gram-positive and Gram-negative bacteria, fungi and viruses, together with cytotoxic activity against tumour cells. Human β-defensins (hBDs) represent a first line of defence against infections caused by a broad spectrum of pathogens. hBD expression occurs in the host tissues most exposed to microorganisms (such as the respiratory and gastrointestinal tracts) and in the cells of the immune system (such as macrophages, lymphocytes and platelets).

A host defence peptide (HDP) has been described in human β-defensin 3 (hBD3), named peptide γ (Nigro E et al., *Sci Rep* 2015; 5:18450, Table 1) because it corresponds to the ancestral motif found in all multiple-disulphide stabilised HDPs, known as the γ-core (Yount N Y, Yeaman M R. *Proc Nat Acad Sci U.S.A* 2004; 101:7363-8 and *Annu Rev Pharmacol Toxicol* 2012; 52:337-60; Yeaman M R, Yount N Y. *Nat Rev Microbiol* 2007; 5:727-40).

Peptide γ retains all the key properties of full-length hBD3 in a simplified structure with a single disulphide, with much easier synthetic accessibility and a lower cost (Nigro E et al., *Sci Rep* 2015; 5:18450; Nigro E et al., *J Pept Sci* 2017; 23:303-10; Falanga A et al., *Molecules* 2017; 22 (7): 1217).

Peptide γ is a small molecule that exhibits most of the biological properties of the natural full-length β-defensins. Beta-defensin analogues useful for the treatment of infections have been described in EP 2 990 415 and EP 2 077 274.

DESCRIPTION OF THE INVENTION

A novel peptide sequence has now been found, characterised by a more substantial change in the γ-core sequence than the full-length hBD3, which improves the activity of peptide γ. The novel peptide has a shorter sequence and a smaller number of sites susceptible to cleavage by serum proteins. The novel peptide according to the invention is therefore stable in blood, is not cytotoxic, performs an effective antibacterial action against both planktonic and sessile bacteria, and also exhibits a bactericidal effect against Gram-positive and Gram-negative MDR bacterial strains.

The peptide according to the invention, hereinafter called "peptide γ2", has the following amino-acid sequence (SEQID1): Ac-CLPKRRQIGKSSTRGRKSCKK-$NH_2$ The peptide can be in oxidised or reduced form, both active.

The invention also relates to the non-acetylated peptide and conventional derivatives thereof.

The peptide according to the invention is useful for the treatment of bacterial infections, in particular infections supported by antibiotic-resistant bacteria untreatable with conventional antibiotic treatments. For that purpose, the peptide or derivatives thereof will be formulated as pharmaceutical compositions with suitable carriers or excipients. The compositions of the invention will preferably be administered parenterally, for example intramuscularly, subcutaneously or intravenously, in the form of injectable solutions in sterile solvents with a peptide concentration ranging from 0.001 to 10% by weight. The dose of peptide will be determined by the skilled person based on preclinical and clinical experiments. Broadly speaking, in view of its favourable pharmaco-toxicological characteristics, the dose could range from 0.1 to 10 mg/Kg/day, depending on the patient's weight, age and severity.

The invention will be described in detail in the following experimental part.

Peptide Synthesis. Synthesis and Purification of Peptide γ2

Peptide γ2 was synthesised by solid-phase peptide synthesis techniques with the (US-SPPS) protocol using Fmoc/tBu (9-fluorenylmethoxycarbonyl/tert-butyloxycarbonyl), as reported in Merlino F et al., *Org Lett* 2019; 21:6378-82. Each peptide was assembled at 100 μmol scale on a Rink Amide AM-PS resin with iterative cycles of Fmoc deprotection and amide coupling reaction. Briefly, the Fmoc protecting group was removed by treating the resin twice with a 20% piperidine solution in DMF (1+1 minute with ultrasound). The coupling reactions were conducted using a molar excess of amino acid and COMU/Oxyma as coupling partner, in the presence of a 6-fold molar excess of DIPEA as base and irradiating in an ultrasonic bath for five minutes. Finally, the peptide was acetylated with acetic anhydride (two equivalents) and DIPEA (4 equivalents) in DMF. The peptide was released from the resin through treatment with an acid cleavage cocktail (TFA/TIS/dithiothreitol 95:2.5:2.5 solution) for three hours, and the mixtures were precipitated in cold ethyl ether, before being centrifuged and evaporated until dry. The crude linear peptide was then oxidised using N-chlorosuccinimide in aqueous solution at the concentration of 1 mM, and then freeze-dried. The crude mixture was purified by preparative reverse-phase HPLC (solvent A: water+0.1% TFA; solvent B: acetonitrile+0.1% TFA; 10 to 60% of solvent B in 25 minutes, flow rate: 10 mL minute-1), and the identity of the purified peaks was then confirmed by ESI-MS analysis (mass range 200-3000 m/z).

Bacterial Strains and Growth Conditions

The antimicrobial activity of peptide γ2 was evaluated versus *Pseudomonas aeruginosa* ATCC 27853, *Escherichia coli* ATCC 13762 and *Staphylococcus aureus* ATCC 6538, and versus multidrug-resistant (MDR) clinical isolates of Methicillin-Resistant *Staphylococcus aureus* (MRSA), extended-spectrum β-lactamase (ESBL)-producing *E. coli, P. aeruginosa* and *Acinetobacter baumannii* complex. The isolates were identified by mass spectrometry using the MALDI (matrix-assisted laser desorption/ionisation) mass spectrometer and the biochemical phenotyping method in a VITEKR 2 bioMérieux system (bioMérieux Italia S.p.a., Bagno a Ripoli, Florence, Italy), according to the manufacturer's instructions. The antibiotic susceptibility profile was evaluated with the VITEKR 2 bioMérieux System. The microorganisms were cultured in broth and agar at 37° C. The media used were BD Brain Heart Infusion broth (BHI) (BD, Franklin Lakes, NJ, USA) and BHI agar (OXOID, Basingstoke, Hampshire, UK), BD Trypticase Soy agar with 5% sheep's blood and MacConkey agar (OXOID, Basingstoke, Hampshire, UK). The isolates were stored frozen at −80° C. in BHI broth supplemented with 10% (v/v) glycerol (Carlo Erba Reagents, Milan, Italy) until use, and the work cultures were activated in the respective broths at 37° C. for 15-18 h.

SYTOX Green Absorption Assay Through Fluorescence Spectroscopy

The effect of peptide γ2 on the membrane integrity of *S. aureus* ATCC 6538 and *P. aeruginosa* ATCC 27853 was evaluated by measuring the extent of intracellular accumulation of SYTOX green (Juba M L, et al. *Biochim Biophys Acta.* 2015; 1848 (5): 1081-91). The cells were harvested halfway through the log phase, washed, and resuspended in 10 mM of phosphate buffer. The final density was adjusted to $5\times10^7$ CFU/mL. The cells were then treated with peptide γ2 (0.625, 1.25, 2.5, 12.5, 25 μM) in the presence of 200 nM SYTOX green (Invitrogen). The fluorescence increase of SYTOX green, a direct measurement of the degree of membrane permeabilisation, was monitored with a fluorescence spectrophotometer. The excitation and emission wavelengths used were 503 nm and 523 nm respectively. 5

Antibacterial Activity Assay and In Vitro Time-Kill Kinetics Assay.

Assays of the antibacterial activity of peptide γ2, in both reduced and oxidised form, were conducted against *P. aeruginosa* ATCC 27853, *E. coli* ATCC 13762, *S. aureus* ATCC 6538 and MDR clinical isolates. The strains were cultured under aerobic conditions in BHI broth at 37° C. and incubated with peptide γ2 for 2 hours at 37° C. Various concentrations of peptide were used, ranging from 1 μM to 128 μM. Each test was conducted in triplicate with three independent cultures. The minimum inhibitory concentration (MIC) and the minimum bactericidal concentration (MBC) of the peptide were determined with a modified version of the Clinical and Laboratory Standards Institute broth microdilution assay, using a final inoculum concentration of $10^5$ CFU/ml, as previously described (Scudiero O et al., *Antimicrob Agents Chemother* 2010; 54:2312-22; Scudiero O et al. *Antimicrob Ag Chemother* 2013; 57:1701-8).

The MIC is indicated by the concentration interval, which comprise the upper growth limit and the first concentration which could not support visible bacterial growth after incubation. The MBC was defined as the lowest concentration at which no viable colonies were observed. The peptide concentrations were 128.0, 64.0, 32.0, 16.0, 8.0, 4.0, 2.0 and 1 μM. For the time-kill studies against the ATCC and MDR strains, the bacteria were cultured in BHI broth until the late log growth phase at 37° C. The bacterial suspensions, containing about 106 CFU/ml (adjusted by the spectrophotometer to $OD_{600\ nm}$), were diluted 1:100 in PBS1× and then incubated at 37° C. with or without the peptide, selected at concentrations corresponding to 1, 2 and 4×MIC (as determined above). At baseline and 1, 2, 3 and 5 hours after incubation, a portion of each sample was harvested, diluted in series in PBS1× and seeded on BHI agar. The plates were incubated for 24-18 hours at 37° C., and the viable bacteria count was conducted by the CFU method. All the data were expressed as mean±SD of three independent experiments.

Antibacterial Assays. Biofilm Formation and Maturation

The biofilm formation test for *S. aureus* ATCC 6538 and *P. aeruginosa* ATCC 27853 was conducted in 96-well plates, as previously reported (Merritt J H, Kadouri D E, O'Toole G A. Growing and analyzing static biofilms. Curr Protoc *Microbiol.* 2005*; Chapter* 1: Unit 1B.1.)

Briefly, the bacteria from overnight cultures were diluted and grown to 0.5 McFarland. The bacteria were diluted 1:100 and plated in each well containing 100 μL of BHI broth. To evaluate the impact of peptide γ2 on biofilm formation, the medium was supplemented with various concentrations of peptide (2.5, 12.5, 25 and 125 μM) and incubated overnight. To evaluate biofilm maturation, the bacteria of the cultures grown overnight were diluted 1:1000, and 5 μL of said bacterial suspensions was added to each well, containing 100 μL of BHI broth, and left to grow overnight. The medium was then removed and replaced with fresh medium containing various peptide concentrations (2.5, 12.5 and 125 μM). At the end of incubation, the medium was removed; the biofilms were washed twice with PBS and stained with crystal violet (1%) for 30 minutes, then resuspended in 200 μL of ethanol. The negative controls were bacteria incubated with medium only. The positive controls were bacteria incubated with medium supplemented with 0.42 μM gentamicin.

The formation of *S. aureus* ATCC 6538 and *P. aeruginosa* ATCC 27853 biofilms was also evaluated by imaging. The medium was then supplemented with various peptide concentrations (2.5, 12.5 and 25 μM) and incubated overnight, and the biofilms were stained with a FilmTracer LIVE/DEAD biofilm viability kit (Invitrogen) according to the manufacturer's instructions. The images were acquired with Cell Discoverer 7, Zeiss.

Cell culture and cytotoxicity studies: MTT assay. Parental HT-1080, HUVEC, SH-SY5Y human fibroblasts (HF) and A549 cells from Culture Cell Lines Facility CEINGE Biotecnologie Avanzate s.c.ar.l., Naples, Italy, and HeLa cells (ATCC CCL-2) stored in liquid nitrogen, were thawed by stirring the vials gently for 2 minutes in a water bath at 37° C. After thawing, the contents of each vial were transferred to a tissue culture flask with an area of 75 cm, and diluted as follows: HT-1080, A549, SH-SY5Y and HeLa with 90% Dulbecco Modified Eagle's Minimal Essential Medium (DMEM), supplemented with 10% foetal bovine serum (Lonza Basel, Switzerland) and 1% L-glutamine; the HUVEC cells were cultured in Eagle Basal Medium (EBM) supplemented with 4% FBS, 0.1% gentamicin, 1 μg/mL hydrocortisone, 10 μg/mL epidermal growth factor and 12 μg/mL bovine brain extract, and used between the third and seventh steps. The HFs were cultured in Dulbecco medium (DMEM) supplemented with 20% fetal bovine serum and 1% l-glutamine.

The cells were incubated for 24 hours at 37° C. in 5% $CO_2$ to allow them to grow and form a single layer in the flask. Cells grown to 80-95% confluency were washed with PBS, treated with 3 mL of trypsin-EDTA 1× solution, diluted, counted and seeded ($4\times10^3$ cells/200 µl per well) in 96-well tissue-culture plates for 24 h in triplicate. The reduction in cell proliferation was evaluated with the 3-[4,5-dimethylthiazol-2-yl]-2,5-diphenyltetrazolium bromide (MTT) assay, which measures metabolic changes. The next day, cells were incubated with or without peptide γ2 according to various schemes: after 24, 48 and 72 hours' incubation at 37° C. at various concentrations, namely 2.5, 12.5, 25 and 125 µM. The adherent cells were stained with the MTT staining solution, namely 20 µL of MTT stock solution diluted 1:10 (5 mg/mL) and incubated for 4 hours. After incubation, the presence of violet crystals, which normally indicate metabolisation of MTT, was evaluated. The medium was then removed (180 µL), and 180 µL of dimethylsulphoxide was added to dissolve the MTT crystals. The specific stain eluted was measured with a spectrophotometer (550 nm). The proliferation index of the untreated cells was compared with that of the negative control (cell plus peptide-free medium). The cell inhibition percentage was determined with the following formula:

% cell inhibition=100−(Absorbance of treated cells/Absorbance of control cells)×100. The values are means+SD of experiments in triplicate. In the same way, the test was repeated on HeLa cells with a peptide γ2 concentration of 40 µM after 6 hours' incubation at 37° C.

The mean percentage cell inhibition values for each cell line at different peptide γ2 concentrations compared with the untreated cells were analysed with One-way ANOVA.

Haemolytic Activity

The haemolytic activity of peptide γ2 was determined against mammal cells using human erythrocytes as previously described (Evans B C et al *J Vis Exp.* 2013; 73: e50166), with the aim of evaluating the safety of the novel peptide. Briefly, whole human blood (from a healthy donor) was centrifuged at 500 rpm for 5 minutes at room temperature to isolate the erythrocytes. Cells were washed twice with a solution of 150 mM NaCl, and erythrocytes were then resuspended in an equal volume of PBS 1×. The sample was stoppered and inverted several times to mix it gently, centrifuged at 500 rpm for 5 minutes, and resuspended in an equal volume of PBS 1×. The erythrocytes were then diluted 1:50, adding 1 mL of cells to 49 mL of PBS1×, and then transferred to 1.5 mL microtubes, together with 2.5, 12.5, 25 and 125 µM of peptide γ2. After incubation at 37° C. for 1 hour, samples were centrifuged and the supernatant was transferred to a 96-well plate to measure their optical density at a wavelength of 450 nm. 20% Triton X-100 (MCC-Medical Chemical Corporation) and PBSIX were used as positive and negative controls respectively. The percentage haemolysis was calculated with the following formula:

% haemolysis=($A_{450}$ treatment with peptide)−($A_{450}$ PBS1×)/($A_{450}$ Triton X-100)−($A_{450}$ PBS1×).

Cell Migration Assays.

Cell migration assays were conducted as previously described (Bifulco K et al., *Mol Cancer* There 2013; 2:1981-93), using Boyden chambers and polyvinylpyrrolidone-free polycarbonate filters with 8 µm pores inserted between a lower and upper compartment. Briefly, the cell suspension ($1\times10^5$ viable cells/mL of serum-free medium) was seeded in each upper chamber. The lower chambers were filled with DMEM only, DMEM containing 10 nM N-formyl-methionyl-leucylphenylalanine peptide (fMLF), as positive control, or increasing peptide γ2 concentration. Incubation was conducted for 4 h at 37° C. in air humidified with 5% $CO_2$. At the end of the assay, the cells on the lower surface of the filter were fixed with ethanol and stained with haematoxylin, and 10 random fields/filter were counted with a 200× magnification. The extent of cell migration was expressed as a percentage of baseline cell migration evaluated in the absence of chemo-attractants, taken as 100% (CTRL).

Cytokine Measurement.

Supernatants for cytokine evaluation were harvested from peripheral blood mononuclear cell cultures (PBMCs) and analysed with the Invitrogen ProcartaPlex bead-based immunoassay (Invitrogen, Thermo Fisher Scientific) using the Luminex instrument platform (Luminex 200, Luminex Corporation), according to the manufacturer's instructions. xPONENT 3.1 software (Luminex) was used for acquisition and analysis of the samples.

Invasion and Protection Assays with Peptide γ2.

The *S. aureus* ATCC 6538, MRSA strain 2 and MRSA strain 3 invasion assays were conducted as previously described (Colicchio R et al., *Antimicrob Agents Chemother* 2015; 59:7637-49; Spinosa M R et al. *Infect Immun* 2007; 75:3594-3603). HeLa cells (ATCC CCL-2) were used for the standard invasion and intracellular viability assays. The cells were cultured in DMEM with 2 mM L-glutamine. The cells were infected at a multiplicity of infection (MOI) of 50 for 1 h, washed twice with PBS1× to eliminate most of the extracellular bacteria, exposed to gentamicin (Sigma-Aldrich) to kill the remaining extracellular bacteria, and then destroyed with saponin (0.5%) to release the intracellular bacteria. To quantify the intracellular staphylococci released by the HeLa cells, the lysed cell suspension was plated on BHI agar, and the number of CFUs was counted the next day. When required, cells were re-incubated in the cell culture medium for various times (3 and 5 hours) after treatment with gentamicin. Treatment with gentamicin was conducted using 105 µM, a concentration 10 times higher than the MIC, for 30 minutes at 37° C. with 5% $CO_2$. Cells were then washed thoroughly with PBS1× to remove the gentamicin and dead extracellular bacteria, and then lysed or re-incubated with medium. To evaluate the protection with the reduced peptide γ2 after treatment with gentamicin, the molecule was added to the sample at the final concentration of 40 M for 1 hour, then washed twice with PBS1×, and finally destroyed with saponin. As the antibacterial activity of the reduced and oxidised peptide γ2 against *S. aureus* ATCC 6538 was very similar (Table 1), only the reduced form was used in the test. In all the experiments, the bacteria were centrifuged (60×g) on the cells to start the assay. The experiments were conducted in triplicate, and the data were expressed as mean±SD.

Results

Antibacterial Activity of Peptide γ2.

To evaluate the antibacterial activity of peptide γ2, in both reduced and oxidised form, various concentrations of each peptide (ranging from 1 to 128 µM) were evaluated against Gram-negative bacteria such as *P. aeruginosa* ATCC 27853 and *E. coli* ATCC 13762, Gram-positive bacteria such as *S. aureus* ATCC 6538, against the corresponding MDR clinical isolates, and also against two clinical strains of *A. baumannii*. The MICs of the peptides were determined by conventional broth microdilution assays. The MIC values ranged from 2 to 4-8 µM for all the microorganisms tested, except for *P. aeruginosa* strain 1 MDR and *A. baumannii* strain 1, which are resistant up to a concentration of 32-64 μM of both forms of peptide (Table 1).

TABLE 1

Antimicrobial activity of peptide γ2

| Isolate | Oxidised peptide γ2 MIC[a] (μM) | Oxidised peptide γ2 MBC[b] (μM) | Reduced peptide γ2 MIC (μM) | Reduced peptide γ2 MBC (μM) |
|---|---|---|---|---|
| *S. aureus* ATCC[c] 6538 | 2 | 8 | 1 | 1-2 |
| MRSA[d] strain 1 | 1 | 2 | 1 | 1 |
| MRSA strain 2 | 2 | 16 | 4-8 | 16 |
| MRSA strain 3 | 2 | 32 | 1 | 4 |
| *E. coli* ATCC 13762 | 1 | 1 | 2 | 2 |
| *E. coli* ESBL[e] strain 1 | 2 | 2 | 2 | 2 |
| *E. coli* ESBL strain 2 | 1 | 32 | 2 | 16 |
| *P. aeruginosa* ATCC 27853 | 4 | 4 | 1 | 1 |
| *P. aeruginosa* MDR[f] strain 1 | 32 | 32 | 64 | 64 |
| *P. aeruginosa* MDR strain 2 | 1 | 32 | 1 | 1 |
| *A. baumannii* MDR strain 1 | 64 | 128 | 64 | 64 |
| *A. baumannii* MDR strain 2 | 4 | 4 | 1 | 1 |

[a]MIC, minimum inhibitory concentration expressed as concentration μM of Peptide;
[b]MBC, minimum bactericidal concentration expressed as concentration μM of Peptide;
[c]ATCC, American Type Culture Collection;
[d]MRSA, methicillin-resistant *Staphylococcus aureus*;
[e]ESBL, extended-spectrum beta-lactamase;
[f]MDR, multidrug-resistant.

Peptide γ2 exerted strong antibacterial effects against *S. aureus* ATCC 6538 and against all the MRSA strains tested. Interestingly, both reduced and oxidised forms of the peptide exhibited strong inhibitory and bactericidal effects against both Gram-positive bacteria (*S. aureus*) and Gram-negative bacteria (*E. coli, P. aeruginosa* and *A. baumannii*), and all the MDR clinical isolates (table 1). Finally, the multidrug-resistant clinical strain 2 of *A. baumannii* exhibited a profile sensitive to both the oxidised and the reduced form, with MIC values of 4 UM and 1 μM respectively.

Evaluation of Antimicrobial Activity of Peptide 2 by the Time-Kill Assay

Figure 2:
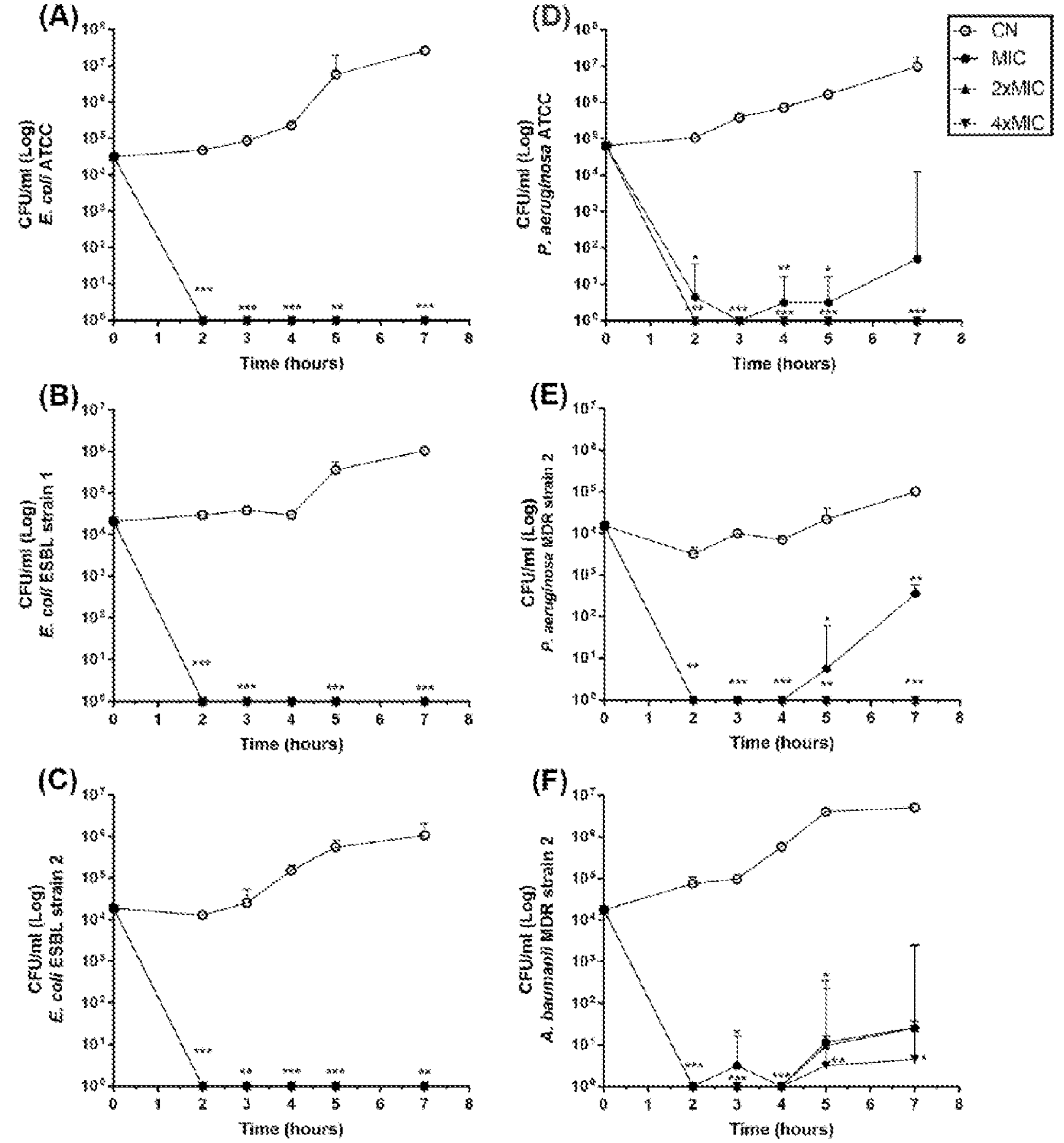

In view of its greater antimicrobial activity, reduced peptide γ2 was selected for the conduct of time-kill studies against representative MDR strains. The ATCC reference strains were also used as internal control. The data relating to the antimicrobial activity of the selected peptide are shown in FIG. 1 and FIG. 2. As shown after 2 hours' incubation with peptide γ2, all the MRSA strains, the ESBL strains of *E. coli* and the corresponding ATCC reference strains, exhibited a total reduction in growth throughout the observation period, at peptide concentrations corresponding to the MIC (FIG. 1 and FIG. 2A-C). However, both strain *P. aeruginosa* ATCC 27853 and the corresponding MDR 2 strain, at the antimicrobial peptide concentration corresponding only to the MIC, exhibited an initial reduction in growth and viability in the first few hours of observation, whereas at longer times (5 and 7 h) a slight resumption in growth and viability was observed for both strains (FIG. 2D, E). Interestingly, at peptide γ2 concentrations corresponding to 2×MIC, there was no growth for either strain (FIG. 2D, E). Finally, for strain *A. baumannii* MDR 2, the assay demonstrated a great reduction in growth and viability after 2 hours' treatment with peptide γ2, and a slight recovery of growth and viability at longer observation times, even at peptide concentrations corresponding to 4×MIC (FIG. 2F).

Permeabilization of *S. aureus* and *P. aeruginosa* Induced by Peptide γ2

Figure 3:
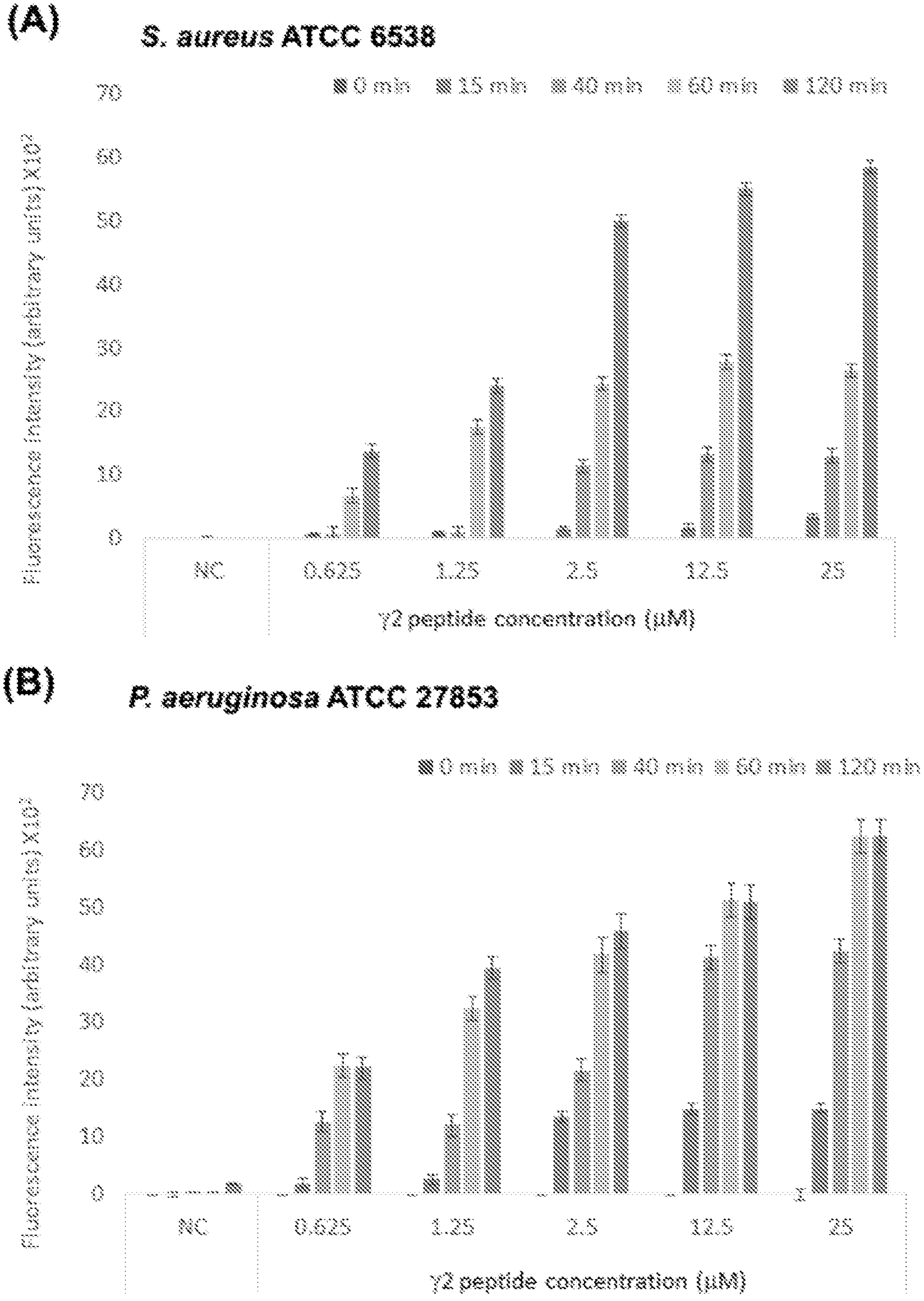

The ability of peptide γ2 to permeabilise *S. aureus* ATCC 6538 and *P. aeruginosa* ATCC 27853 was evaluated (FIGS. 3A and B). Permeabilization by SYTOX Green was evaluated 15, 40 and 60 min after addition of SYTOX Green and peptide γ2 at various concentrations (0.625, 1.25, 2.5, 12.5 and 25 μM). Peptide γ2 caused an increased influx of SYTOX Green after only 15 minutes' incubation for *P. aeruginosa*, whereas for *S. aureus*, it was evident after 40 minutes' incubation. The peptide already effectively permeabilised both bacteria at a dose of 1.25 μM to a dose-dependent extent, with the most significant effect at the highest dose and maximum exposure time.

Evaluation of Antimicrobial Activity of Peptide γ2 on Biofilm Formation and Maturation.

In response to various stresses, bacteria can form biofilms, a community of microbes enclosed in a self-produced matrix which often contains polysaccharides, DNA and proteins and adheres to surfaces, giving rise to chronic infections resistant to antimicrobial treatment and antibiotics, which are particularly difficult to treat.

Figure 4:
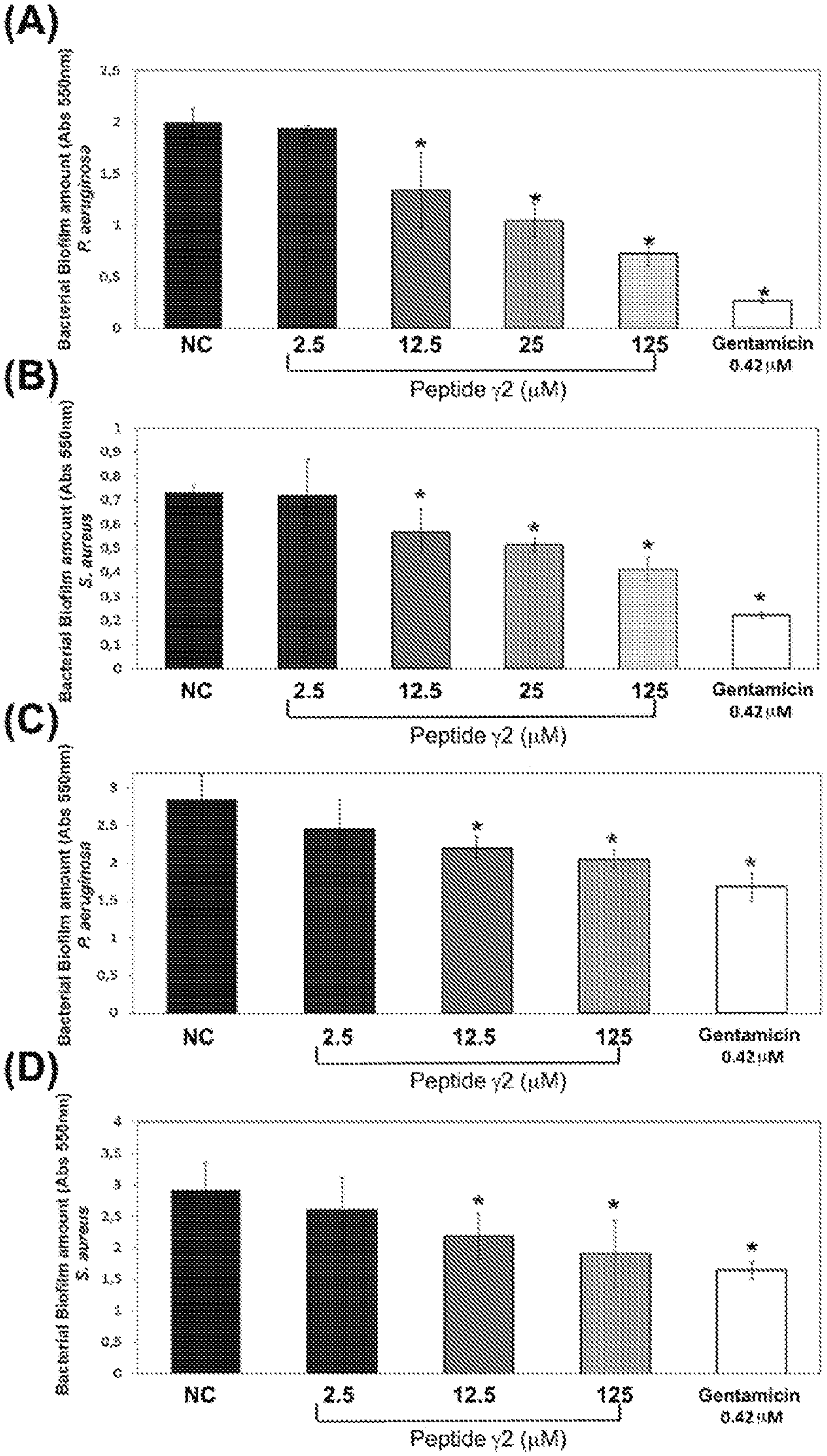

The MIC for peptide γ2 against planktonic *S. aureus* ATCC 6538 and *P. aeruginosa* ATCC 27853 ranged from 1-2 μM for both the reduced form and the oxidised form. The same peptide was therefore tested for inhibition of biofilm formation and maturation (FIG. 4). The peptide significantly inhibited biofilm formation and maturation by both *S. aureus* ATCC 6538 and *P. aeruginosa* ATCC 27853 (FIG. 4), at concentrations slightly higher than those of the MIC for planktonic bacteria. The activity of peptide γ2 was dose-dependent, with the maximum activity at 125 μM; in particular, the activity of peptide γ2 was very strong during the biofilm formation stage (FIGS. 4A and B). Gentamicin was used as control.

Figure 5:
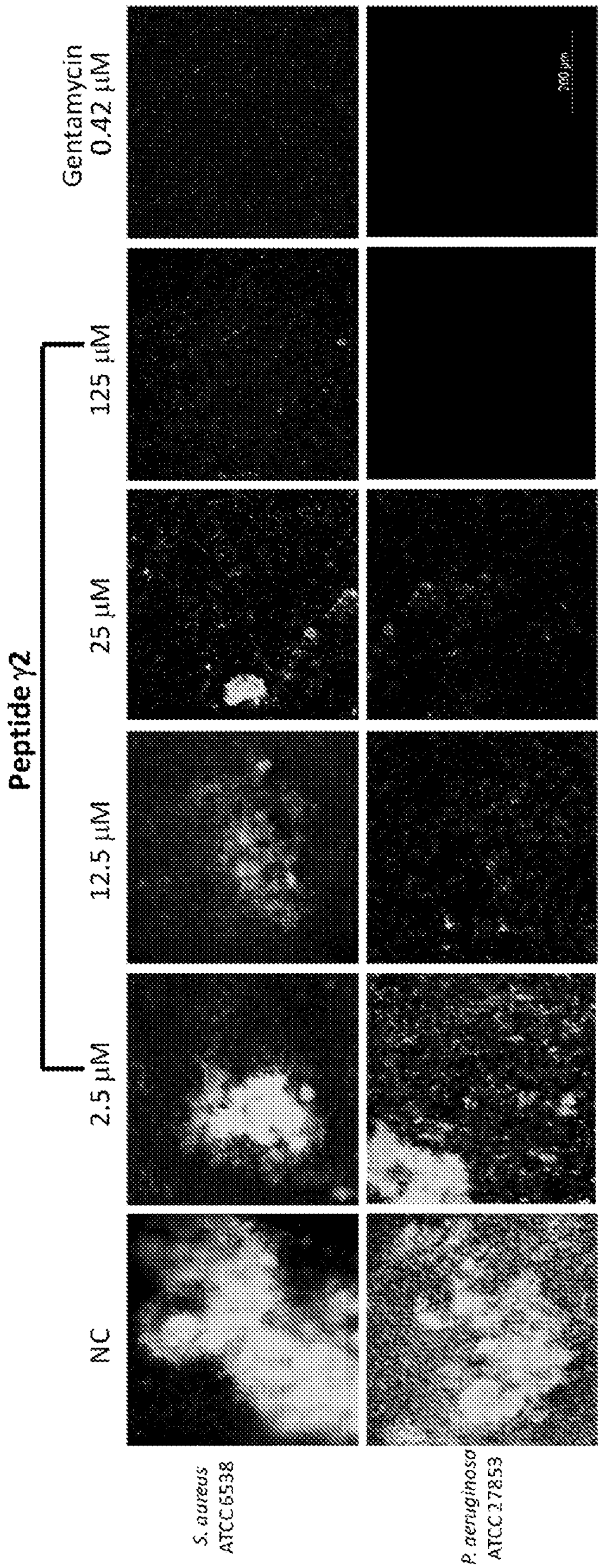
Figure 6:
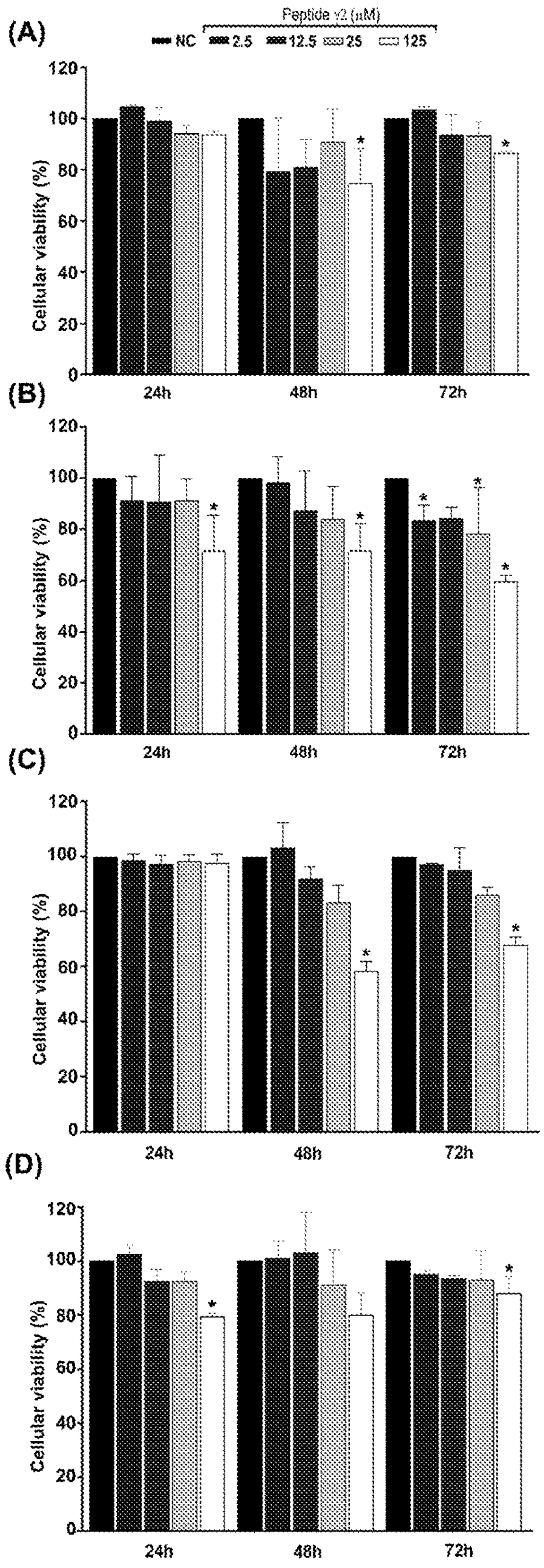
Figure 7:
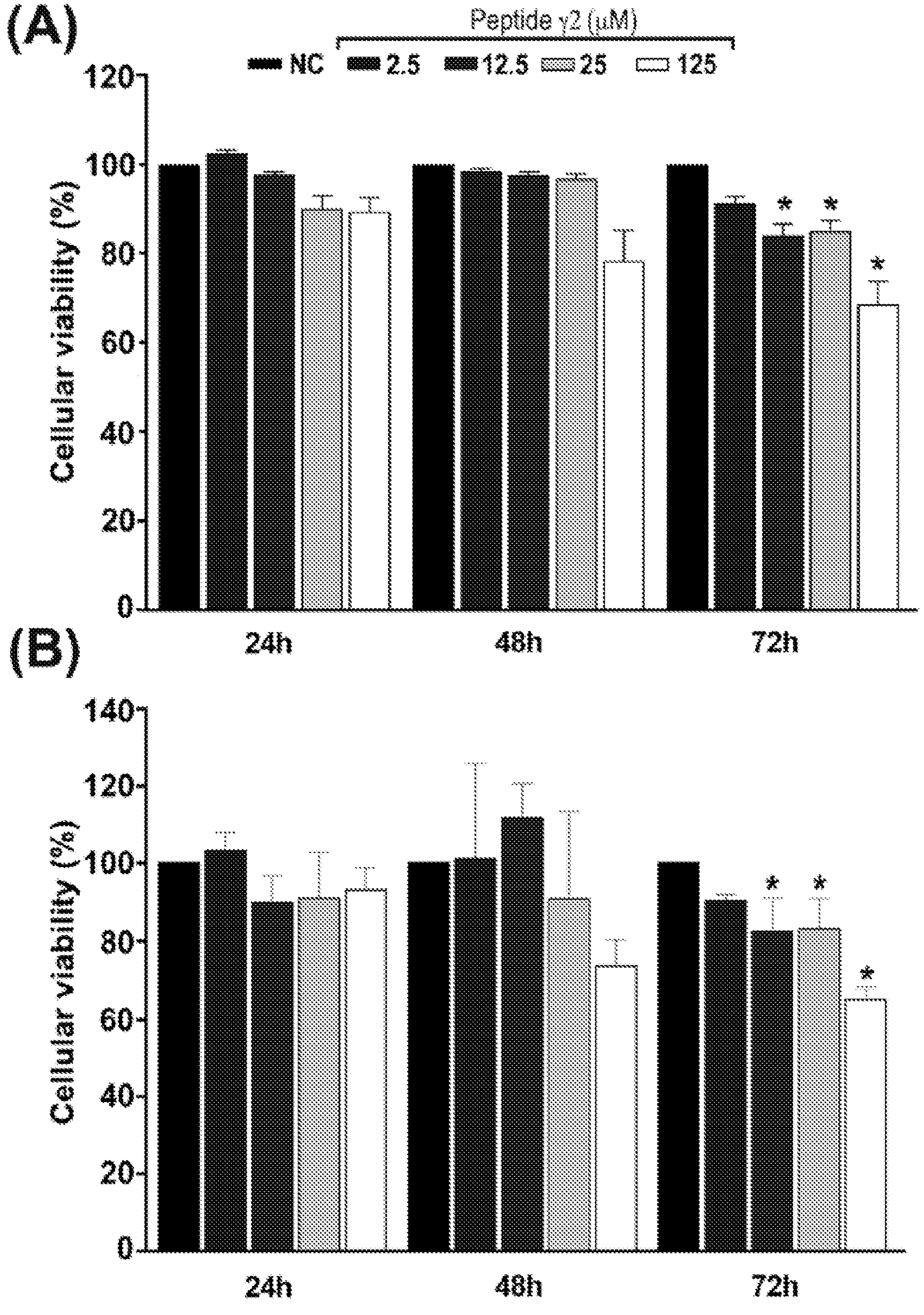

Moreover, to evaluate whether peptide γ2 reduces the volume of *S. aureus* ATCC 6538 and *P. aeruginosa* ATCC 27853 biofilms, the biofilms formed by both bacterial strains after 24 h of static culture were stained with a LIVE/DEAD stain and imaged by Cell Discoverer 7, Zeiss (FIG. 5). On examination of the images, the biofilms formed by untreated bacteria (both *S. aureus* and *P. aeruginosa*) were considerably thicker and larger in volume than those formed by the bacteria treated with peptide γ2. The inhibition of biofilm formation induced by peptide γ2 was dose-dependent; it was already evident for the smallest dose (2.5 μM), but the greatest effect was obtained when 125 μM of peptide was used.

Evaluation of Cytotoxicity Activity of Peptide γ2.

The cytotoxic activity of peptide γ2 was tested on HT-1080, A549, HeLa, SH-SY5Y, HUVEC and HF cells at concentrations of 2.5, 12.5, 25.0 and 125 μM, with exposure times of 24, 48 and 72 hours. FIGS. 6A-D and 7A-B respectively show the percentage viability values of HT-1080, A549, SH-SY5Y and HeLa, and the primary cell models, HUVEC and HF cells, exposed to peptide γ2.

The peptide was non-toxic at concentrations of 2.5, 12.5 and 25 μM after 24 and 48 hours exposure for all cell lines tested. After 72 hours incubation, the peptide had reduced cell viability by about 20%, even at the lowest concentrations, only in the A549, HUVEC and HF cells. Conversely, for the HeLa and HT1080 cells, viability remained high at low peptide concentrations, even with lengthy exposure times. However, the higher concentration of peptide γ2 reduced cell viability in all cell types, significantly after only 24 hours for the A549 and HeLa cells, and after 48 hours for the SH-SY5Y cells.

This series of experiments therefore demonstrates that peptide γ2 does not induce significant cytotoxic effects in vitro when used at a concentration of 2.5, 12.5 or 25.0 μM for up to 48 consecutive hours of exposure in all the cell lines analysed.

Figure 8:
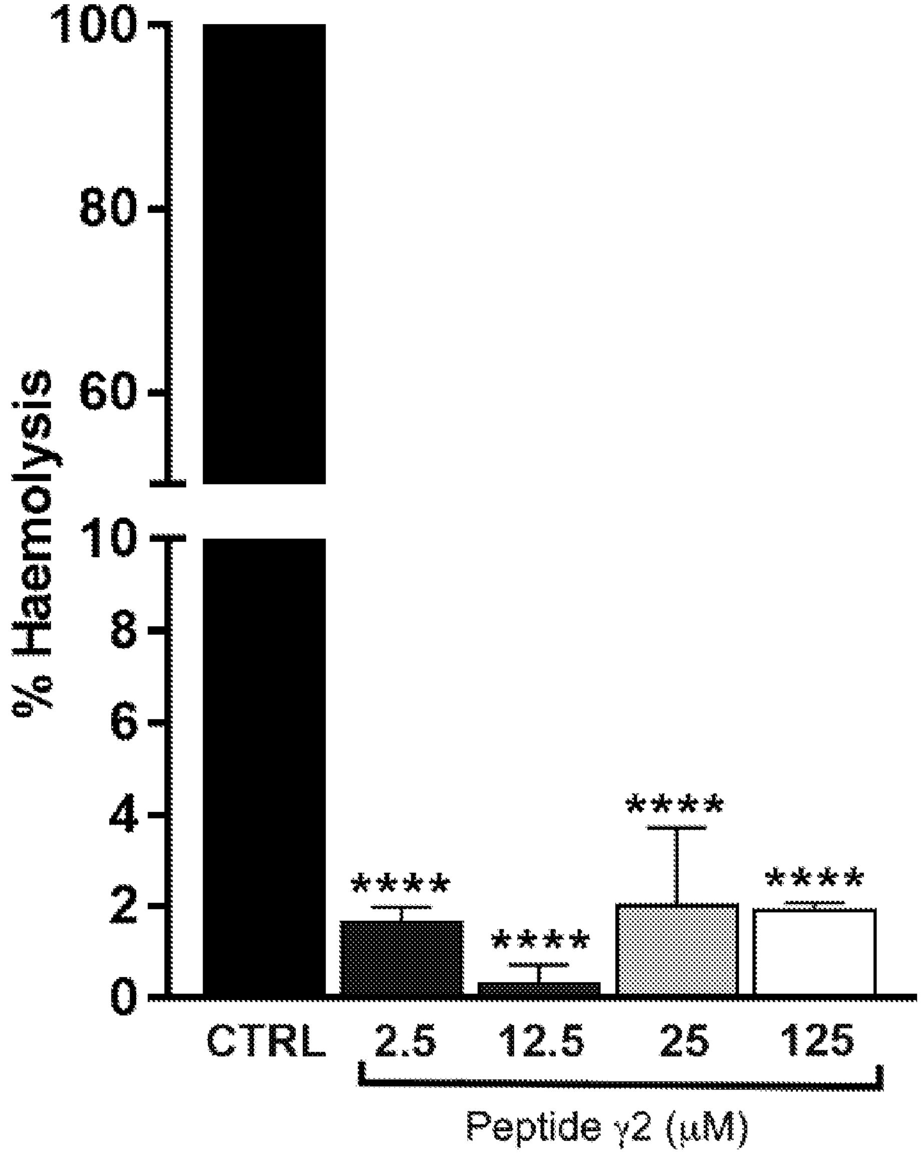

To rule out a cytotoxic activity of the peptide, haemolytic activity against red blood cells was evaluated, also as an indicator of the safety of peptide γ2. The peptide proved not to cause haemolysis, even at the maximum concentration of 125 μM, with less than 2-3% haemolysis observed (FIG. 8).

Effect of Peptide γ2 on HT-1080, A549 and HUVEC Cell Migration.

Figure 9:
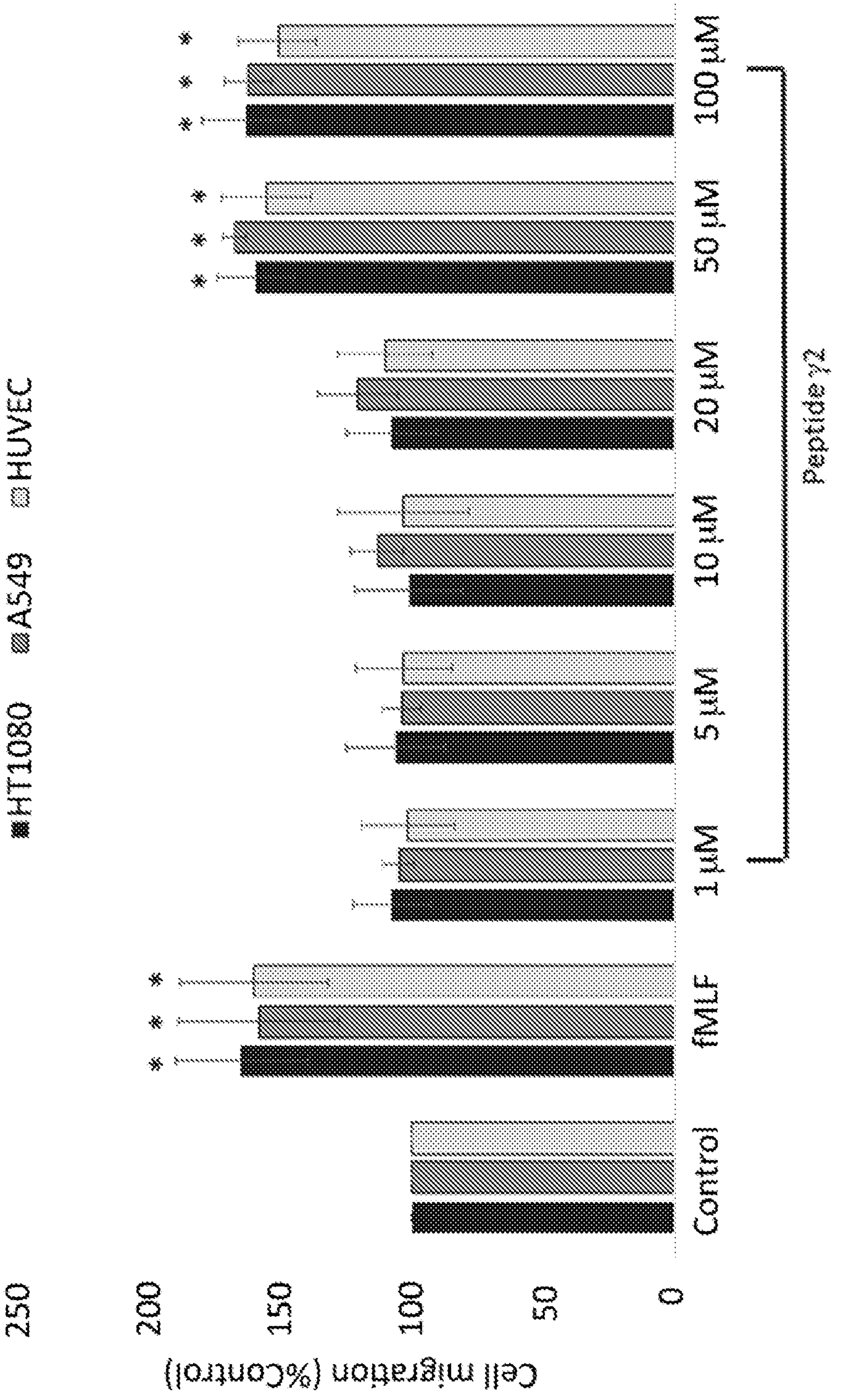

To evaluate whether peptide γ2 acts as a chemotactic factor, cell migration assays were conducted in Boyden chambers using HT-1080 and A549 tumour cells, and primary HUVEC endothelial cells. Cells were migrated towards the peptide of bacterial origin fMLF, used as positive control, or increasing concentrations of peptide γ2. Unsurprisingly, 10 nM fMLF triggered considerable cell migration of HT-1080, A549 and endothelial cells, reaching 167%, 153% and 166% of the baseline cell migration respectively. In all cases, low concentrations of peptide γ2 gave rise to a slight chemotactic effect, which increased when the peptide was used at a concentration of 50 μM or 100 μM (FIG. 9). The degree of HT-1080, A549 and endothelial cell directional migration triggered by 50 μM of peptide γ2 was very similar to that promoted by fMLF, reaching 158%, 169% and 156% of the baseline cell migration respectively. At the concentration of 100 μM, peptide γ2 did not further increase directional cell migration (FIG. 9).

Peptide γ2 Induces Cytokine Secretion in Peripheral Blood Mononuclear Cells (PBMC)

Figure 10:
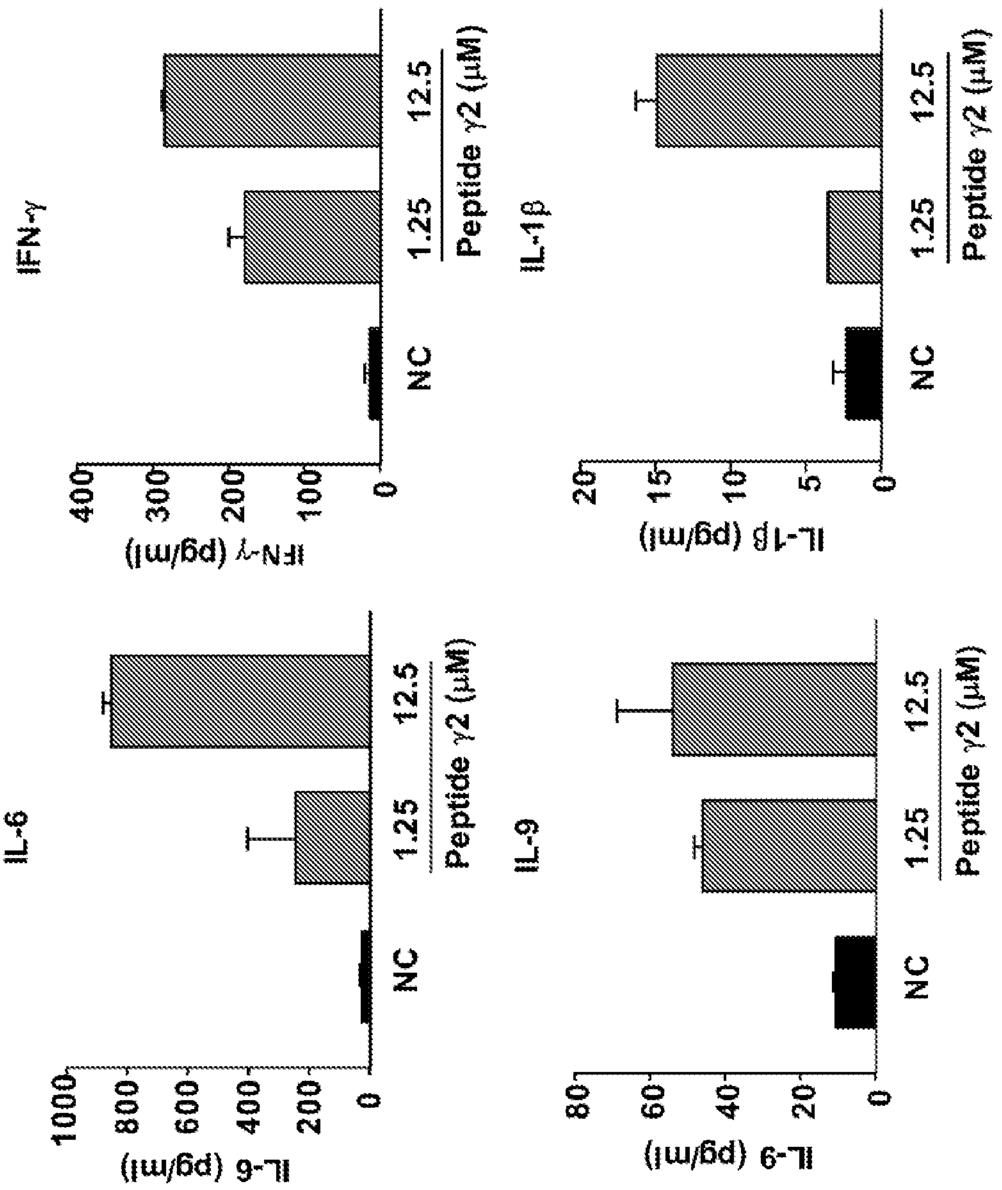

To evaluate whether peptide γ2 can stimulate cytokine secretion by human PBMCs, we examined the secretion of a panel of 20 cytokines in PBMCs after treatment with peptide γ2. Two doses of the peptides (1.25 and 12.5 μM) were used to stimulate PBMCs isolated from healthy donors, and the following cytokines were assayed in media after 18 hours: granulocyte-macrophage colony stimulating factor (GM-CSF), interferon (INF)-γ, interleukin (IL)-1β and IL-2, IL-4, IL-5, IL-6, IL-7, IL-8, MCP-1, IL-9, IL-10, IL-12, IL-13, IL-15, IL-17A, IL-18, IL-21, IL-22 and IL-23. As shown in FIG. 10, INF-γ, IL-1, IL-6 and IL-9 secretion is up-regulated in PBMCs after treatment with peptide γ2, suggesting its ability to induce antigen-independent secretion of pro-inflammatory cytokines.

Protection by Peptide γ2 Against Infection of HeLa Cells.

Figure 11:
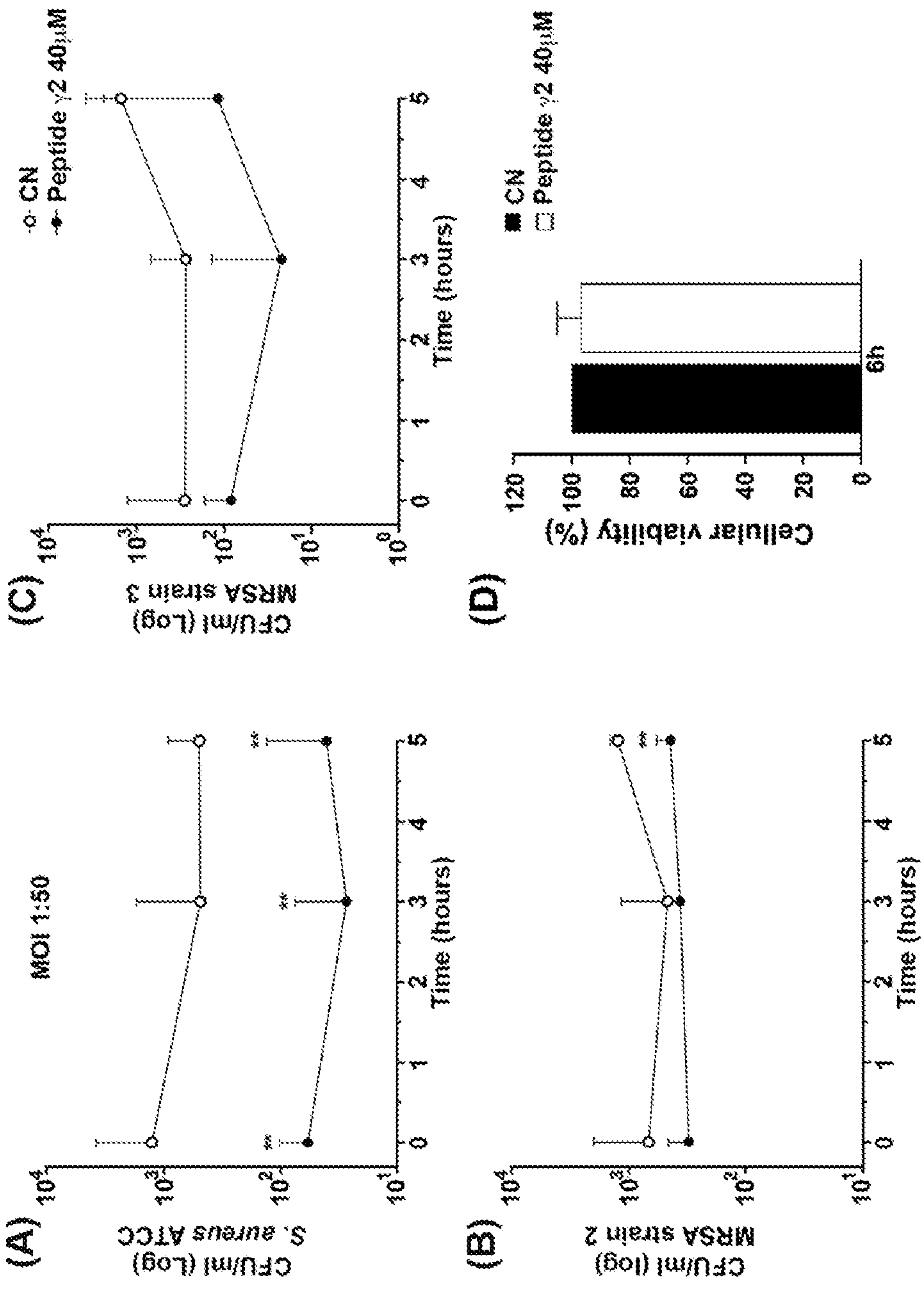

To evaluate whether peptide γ2 protects eukaryotic cells against bacterial infection, invasion assays were conducted in HeLa cells with *S. aureus* ATCC 6538 and MRSA strain 2 and strain 3. For this purpose, we evaluated the survival and growth of selected strains of *S. aureus* after entry into the human cell line HeLa, with or without reduced peptide γ2 at a final concentration of 40 μM. The Hela cells and bacteria were used at a MOI of 1:50 (FIG. 11A-C). After 1 hour incubation followed by treatment with gentamicin to eliminate extracellular and/or adherent bacteria, cells were treated with peptide γ2 for 1 h. At the end, the number of viable intracellular bacteria was determined by the CFU method. The results demonstrated a great reduction in viable intracellular bacteria of the wild-type strain and the MRSA 3 strain in the presence of peptide γ2 at all the times tested, while for the MRSA 2 strain a bacteriostatic effect was exhibited, with inhibition of bacterial replication. These findings suggest that the novel analogue hBD3 can efficiently internalise in human cells and that it exhibits strong antibacterial activity also during the intracellular phase of invasion. Moreover, to rule out a possible cytopathic effect on HeLa cells at the peptide γ2 concentration used in the protection assays, the MTT assay was also conducted at a peptide γ2 concentration of 40 μM for 6 hours, confirming 97% cell viability compared with the control cells (FIG. 11D).

The invention claimed is:

1. A peptide having the sequence Ac-CLPKRRQIGKS STRGRKSCKK(SEQ ID NO:1)-$NH_2$.

2. A pharmaceutical composition comprising the peptide according to claim 1 and a pharmaceutically acceptable carrier or excipient.

3. A method of treating a bacterial infection in a patient in need thereof, said method comprising administering a pharmaceutical composition comprising Ac-CLPKRRQIGKSSTRGRKSCKK(SEQ ID NO: 1) -$NH_2$ in combination with a pharmaceutically acceptable carrier or excipient.

4. The method according to claim 3, wherein the bacterial infection is caused by antibiotic-resistant bacteria.

* * * * *

```
                              SEQUENCE LISTING

Sequence total quantity: 1
SEQ ID NO: 1           moltype = AA  length = 21
FEATURE                Location/Qualifiers
REGION                 1..21
                       note = synthetic peptide
MOD_RES                1
                       note = ACETYLATION
source                 1..21
                       mol_type = protein
                       organism = synthetic construct
SEQUENCE: 1
CLPKRRQIGK SSTRGRKSCK K                                       21
```